(12) United States Patent
Grevious

(10) Patent No.: US 7,871,411 B2
(45) Date of Patent: Jan. 18, 2011

(54) STERNAL CLOSURE DEVICE

(76) Inventor: Mark Grevious, 849 W. Ohio St., Unit #1, Chicago, IL (US) 60622

(*) Notice: Subject to any disclaimer, the term of this patent is extended or adjusted under 35 U.S.C. 154(b) by 635 days.

(21) Appl. No.: 11/498,393

(22) Filed: Aug. 3, 2006

(65) Prior Publication Data

US 2007/0038218 A1 Feb. 15, 2007

Related U.S. Application Data

(60) Provisional application No. 60/708,085, filed on Aug. 12, 2005.

(51) Int. Cl.
*A61B 17/56* (2006.01)

(52) U.S. Cl. .................... 606/60; 606/251; 606/252; 606/253; 606/250; 606/216; 606/257; 606/258; 606/264; 606/286; 606/74; 606/324; 606/326

(58) Field of Classification Search ............ 606/60, 606/213, 216, 250–3, 256–8, 264, 276, 280, 606/286, 324, 326
See application file for complete search history.

(56) References Cited

U.S. PATENT DOCUMENTS

| 268,632 | A | * | 12/1882 | Danforth ................ 606/218 |
|---|---|---|---|---|
| 3,473,528 | A | | 10/1969 | Mishkin et al. |
| 3,693,616 | A | * | 9/1972 | Roaf et al. ............. 606/250 |
| 3,926,193 | A | * | 12/1975 | Hasson ................ 606/218 |
| 4,201,215 | A | | 5/1980 | Crossett et al. |
| 4,279,248 | A | | 7/1981 | Gabbay |
| 4,583,541 | A | | 4/1986 | Barry |
| 5,139,498 | A | | 8/1992 | Astudillo Ley |
| 5,358,510 | A | * | 10/1994 | Luscombe et al. ......... 606/220 |
| 5,722,976 | A | * | 3/1998 | Brown .................. 606/281 |
| 5,843,126 | A | * | 12/1998 | Jameel ................. 606/220 |
| 6,051,007 | A | | 4/2000 | Hogendijk et al. |
| 6,217,580 | B1 | | 4/2001 | Levin |
| 6,302,899 | B1 | | 10/2001 | Johnson et al. |
| 6,432,108 | B1 | * | 8/2002 | Burgess et al. ........... 606/252 |
| 6,540,769 | B1 | | 4/2003 | Miller, III |
| 6,712,821 | B2 | | 3/2004 | Gabbay |
| 2006/0122611 | A1 | * | 6/2006 | Morales et al. ............. 606/72 |
| 2009/0118775 | A1 | * | 5/2009 | Burke .................. 606/324 |
| 2009/0234358 | A1 | * | 9/2009 | Morales et al. ............. 606/60 |

* cited by examiner

*Primary Examiner*—Thomas C Barrett
*Assistant Examiner*—David W Bates
(74) *Attorney, Agent, or Firm*—Thomas C. Saitta

(57) ABSTRACT

A sternal closure device for securing and retaining longitudinally divided halves of a sternum, the device having two sets of anterior and posterior longitudinally extended brace members with brace joining mechanisms extending through the sternal halves to join the anterior brace members to the posterior brace members, such that the sternal halves are compressed between the anterior and posterior brace members, and transverse bridging members that laterally connect the two sets of brace members, with securing mechanisms to retain the two sets of brace members in a contracted configuration with the sternal halves in abutting relation.

23 Claims, 6 Drawing Sheets

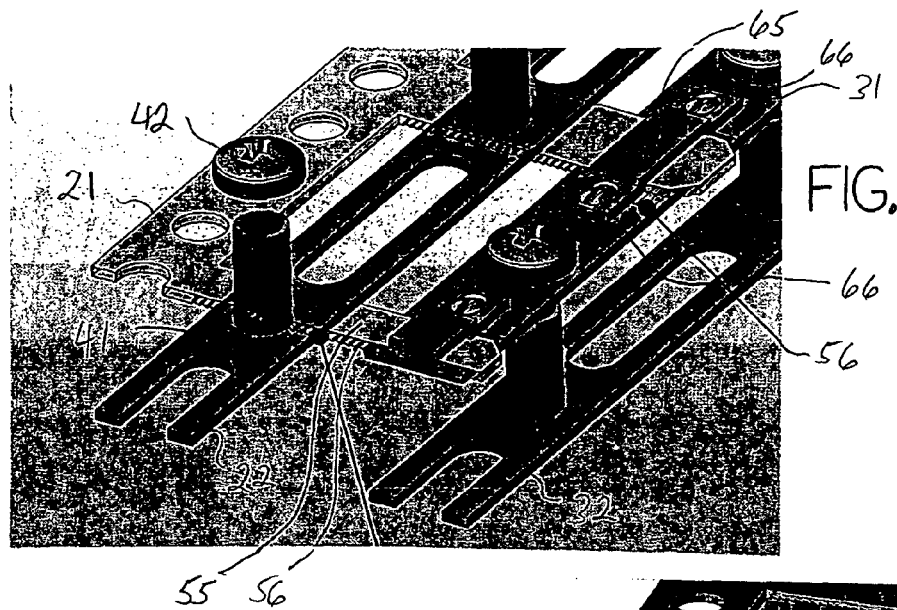
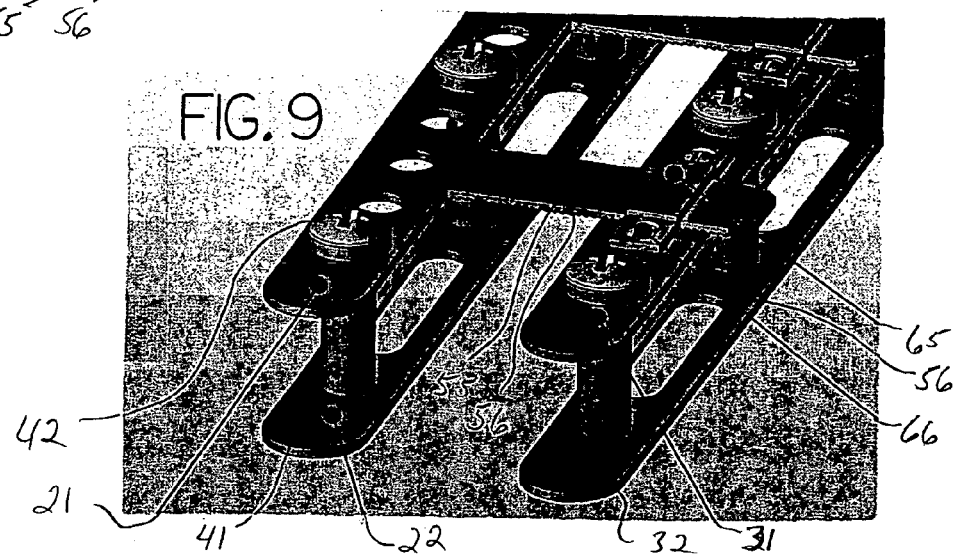
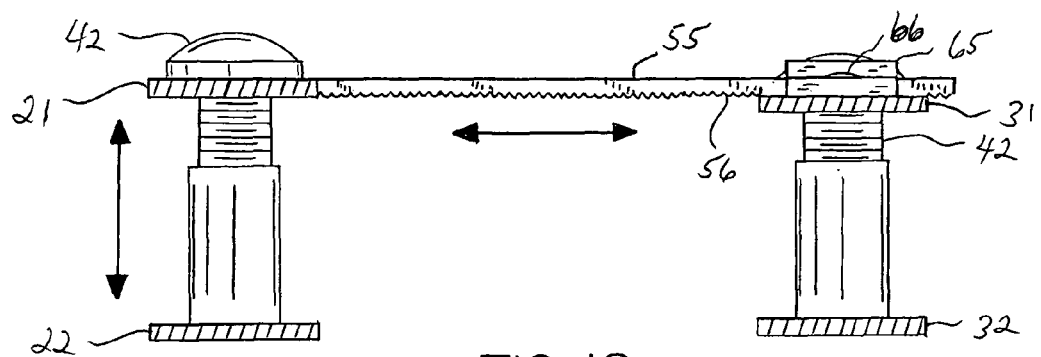

STERNAL CLOSURE DEVICE

This application claims the benefit of U.S. Provisional Patent Application Ser. No. 60/708,085, filed Aug. 12, 2005.

BACKGROUND OF THE INVENTION

This invention generally relates to devices used to rejoin a human sternum that has been longitudinally severed, and more particularly relates to such devices that function in a clamping manner to retain the two severed sternum portions in a closed and abutting relationship post-operatively for an extended period of time such that healing of the sternum may occur.

It is often necessary in surgical operations to longitudinally sever the patient's sternum so that the ribs may be spread to provide access to internal organs such as the heart. It is then necessary to secure the bisected sternum halves together for post-operative recovery. Various closure techniques are used to accomplish this task. For example, holes may be drilled into the sternum halves and suture material passed through and tightened to cinch the sternum halves together. Apertured plates may be added to further rigidify the sternum post-operatively, with the suture material being passed through the apertures in the plate and the sternum. Encircling members may be wrapped around the sternum and tightened. Toothed bridging members extending across the cut line may be pressed into the sternum surfaces and/or secured with threaded rods extending between the sternal halves.

Another sternal closure technique involves the use of clamps having hook-like projections or engagement members on both ends, the clamp being positioned laterally relative to the sternal incision with the projections being disposed between adjoining rib pairs. The clamp is then contracted or compressed to shorten the device and force the sternal halves together, the clamp typically comprising two members joined in a telescoping manner. Locking or securing means, either permanent or releasable, maintain the clamp in the contracted configuration.

Examples of such techniques and devices are described in U.S. Pat. No. 3,473,528 to Mishkin et al., U.S. Pat. No. 4,201,215 to Crossett et al., U.S. Pat. No. 4,279,248 to Gabbay, U.S. Pat. No. 4,583,541 to Barry, U.S. Pat. No. 5,139,498 to Astudillo Ley, U.S. Pat. No. 6,051,007 to Hogendijk et al., U.S. Pat. No. 6,217,580 to Levin, U.S. Pat. No. 6,302,899 to Johnson et al., U.S. Pat. No. 6,540,769 to Miller, III, and U.S. Pat. No. 6,712,821 to Gabbay.

Problems occur with these techniques and devices when the sternum is relatively weak due to age, illness, etc., such that the bone material cannot bear the localized stresses imparted by the sutures, bone anchors or clamping devices of the known systems. Closure techniques that require suturing are excessively time consuming. Bracing devices that are not adjustable either in depth or width cannot be properly adapted to correspond to conditions of a particular patient.

It is an object of this invention to provide a sternal closure device having the functionality of a contractible sternal clamp, such that the sternal halves may be quickly and easily forced together and retained in position, but providing greater reinforcement and rigidity to the severed sternum, and which is also effective in circumstances where the sternum is in a weakened condition. It is an object to provide such a sternal closure device wherein longitudinal brace or scaffold members are secured to the sternal halves with the sternal halves retained in a force-spreading, compressive manner, the longitudinal brace members being joined by transversely extending bridging members, the bridging members having locking or securing means, preferably releasable, such that when the longitudinal bridging members and sternal halves are compressed together, the locking or securing means maintain the device in the contracted or tightened configuration with the sternal halves abutting.

SUMMARY OF THE INVENTION

The invention is in general a sternal closure device for post-operatively closing, securing and supporting a patient's sternum that has been longitudinally severed, i.e., bisected from top to bottom. The device comprises two laterally positioned assemblies of longitudinally extending brace or scaffold members, each assembly comprising a posterior brace member and an anterior brace member. The posterior and anterior brace members of each assembly are joined together by brace joining means extending through apertures or bores cut into the bone material of the left or right sternal half such that the sternal half is compressed, i.e., sandwiched, between the anterior and posterior brace member. The separation distance between the posterior and anterior brace members is adjustable such that the device is adaptable for use with sternums of differing thicknesses.

The left and right brace assemblies are joined together by transverse bridging members that connect the anterior brace members and span the sternal separation line or kerf. The transverse bridging members enable the separation distance between the left and right brace member sets to be adjusted, such that the two sets can be forced together to abut the sternal halves. The transverse bridging members are provided with locking or securing means, preferably releasable, such that the sternal halves are retained in abutment.

BRIEF DESCRIPTION OF THE DRAWINGS

FIG. 8 is a partial view of the device of FIG. 7, better illustrating the chosen embodiment for the securing means, and showing the longitudinal brace members prior to being compressed together.

FIG. 9 is a partial view similar to FIG. 8, showing the longitudinal brace members in the compressed configuration.

FIG. 10 is an end view of the device taken along line X-X of FIG. 7, the longitudinal brace members being shown in cross-section to better expose the brace joining means.

DETAILED DESCRIPTION OF THE INVENTION

Figure 1:
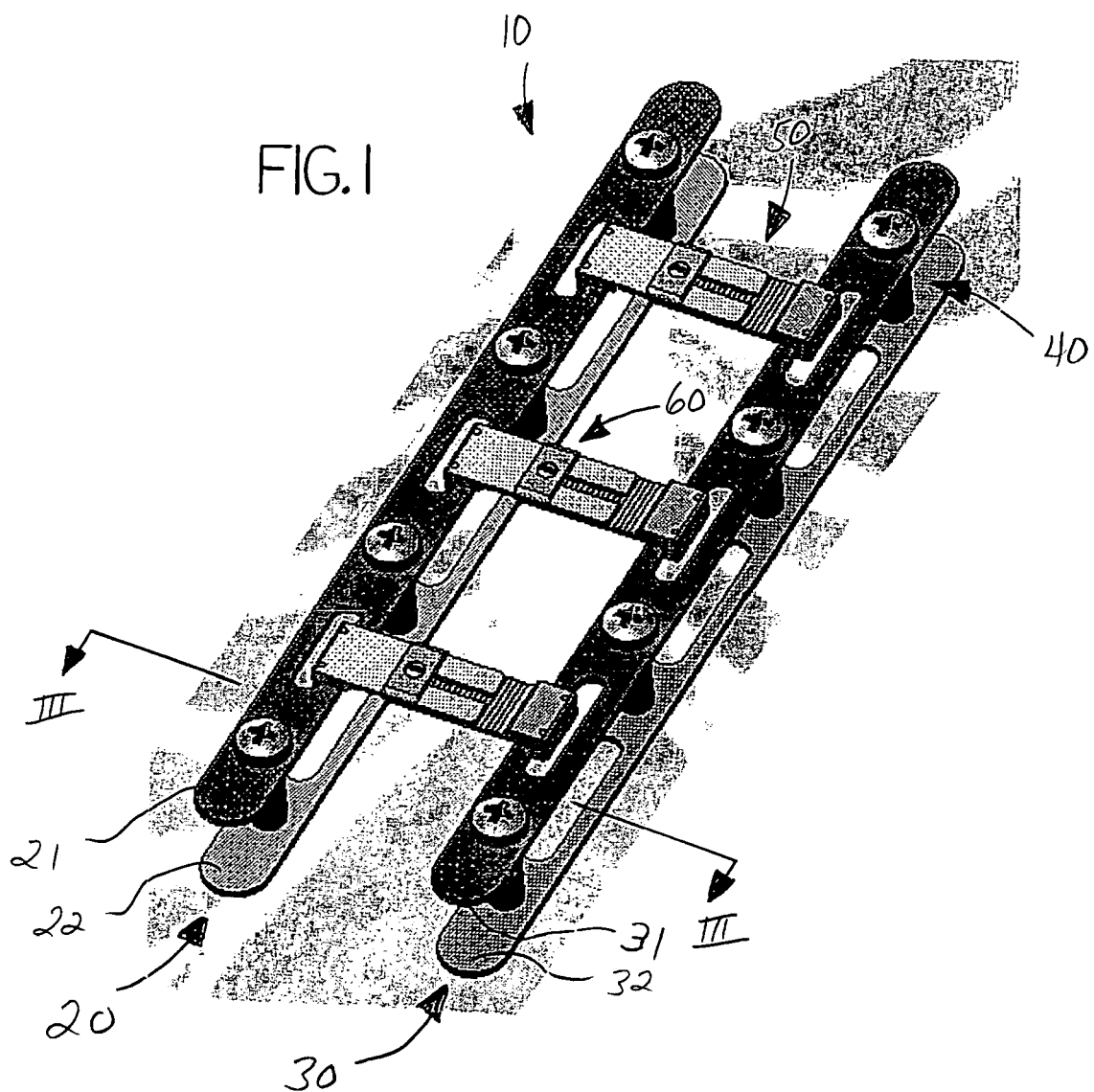
FIG. 1 is a perspective view of one embodiment of the sternal closure device.
Figure 2:
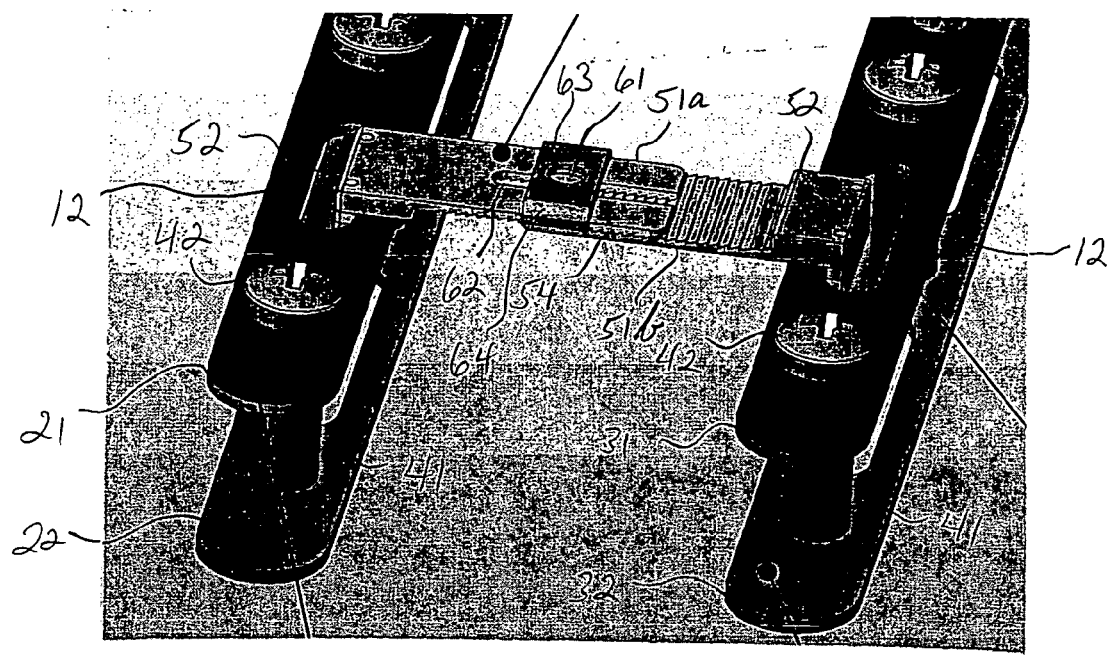
FIG. 2 is a partial view of the device of FIG. 1, better illustrating the chosen embodiment for the securing means.
Figure 3:
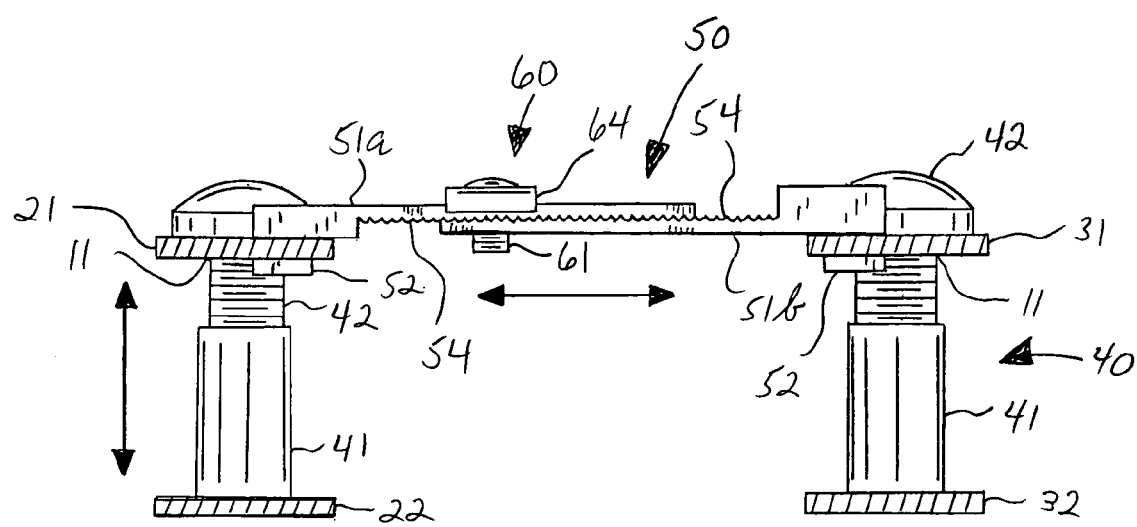
FIG. 3 is an end view of the device taken along line III-III of FIG. 1, the longitudinal brace members being shown in cross-section to better expose the brace joining means.

With reference to the drawings, the invention will now be described in detail with regard for the best mode and the preferred embodiment. The invention is in the most general sense a sternal closure device used to close, secure and support a sternum post-operatively, the sternum having been longitudinally severed or bisected into left and right lateral halves to provide access to the interior of the chest. For ease of reference, the terms left and right as used herein shall mean the directions as seen by an observer facing the sternum of the patient, such that the right brace assembly and the right sternal half are disposed to the patient's sinistral side, while the left brace assembly and the left sternal half are disposed to the patient's dextral side.

A first embodiment of the invention is illustrated in FIGS. 1 through 6. The sternal closure device 10 comprises two sets of laterally disposed brace assemblies 20 and 30, with left brace assembly 20 comprising a longitudinally extended top or anterior brace member 21 and a longitudinally extended bottom or posterior brace member 22 joined by brace joining means 40, and with right brace assembly 30 comprising a longitudinally extended top or anterior brace member 31 and a longitudinally extended bottom or posterior brace member 32 joined by brace joining means 40. Brace joining means 40 comprise members adapted to be positioned within apertures or bores provided in the sternal halves 91/92, such that the brace joining means 40 pass through the sternal halves 91/92. Preferably, the brace joining means 40 are such that the separation distance between the anterior brace members 21/31 and the posterior brace members 22/32 is adjustable to account for differences in the thickness of various sternums 90, such that the sternal half 91 is compressed between the anterior and posterior brace members 21/22, and such that the sternal half 92 is compressed between the anterior and posterior brace members 31/32. Preferably, the brace joining members 40 comprise internally threaded sleeve or post members 41 extending anteriorly from the posterior brace members 22/32, with the sleeve members 41 receiving threaded fasteners 42 that are disposed through fastener receiving apertures 11 correspondingly positioned in the anterior brace members 21/31. In this manner the securing forces are not concentrated in localized points or areas, such as would occur with bone anchor screws or the like, but instead are dispersed along the lengths of the brace assemblies 20/30. Likewise, no stresses are imparted to the ribs 93.

Figure 4:
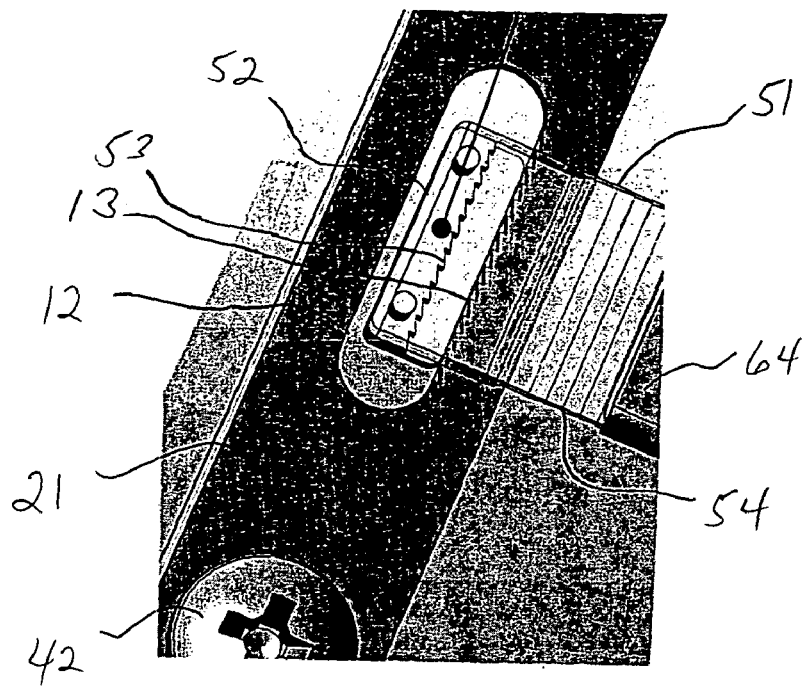
FIG. 4 is a partial view of the interlocking means for the transverse bridging members.
Figure 5:
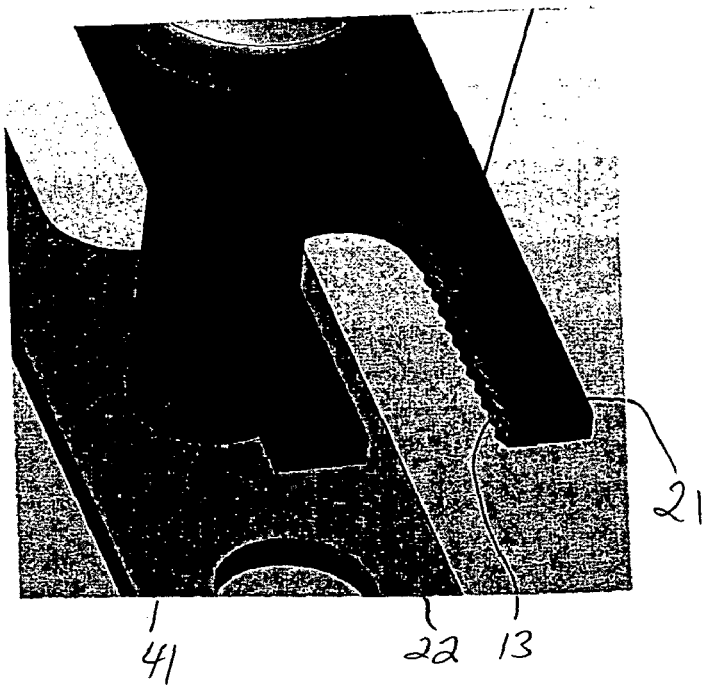
FIG. 5 is a partial view showing a bridging member receiving slot.
Figure 6:
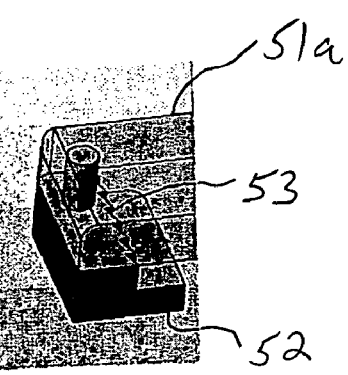
FIG. 6 is a partial view showing the hook end of a bridging member.
Figure 7:
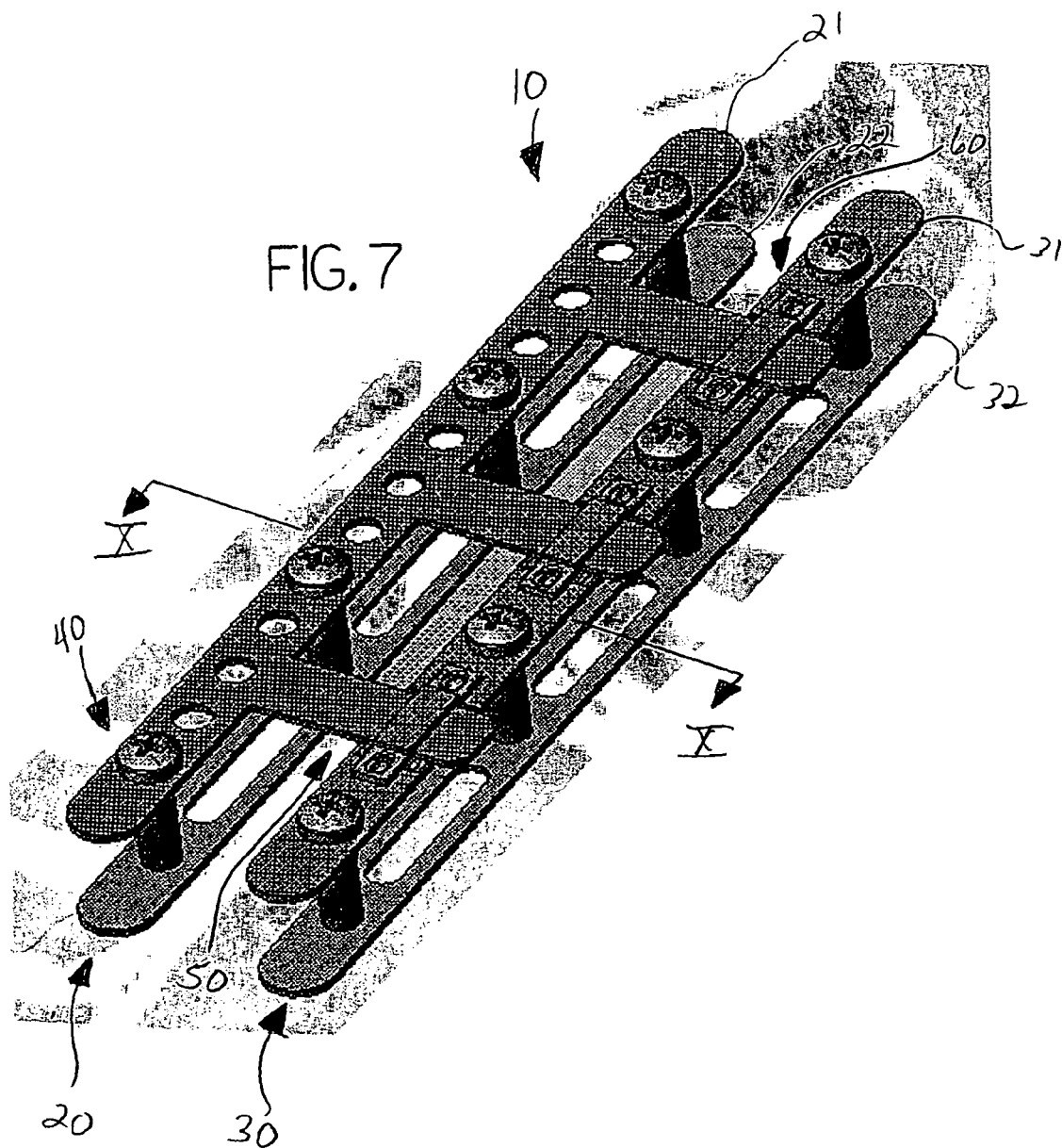
FIG. 7 is a perspective view of another embodiment of the sternal closure device, showing an alternative embodiment for the bridging members.

The anterior brace members 21/31 and the posterior brace members 22/32 are composed of a relatively rigid, bio-compatible metal or similar material such that support and rigidity are imparted to the sternal halves 91/92. The laterally disposed left and right brace assemblies 20/30 are connected to each other by transverse bridging means 50, whereby the longitudinal juxtapositioning of the two brace assemblies 20/30 is held in fixed relation, while the lateral distance between the two brace assemblies 20/30 is variable. As shown in the embodiment of FIGS. 1 through 6, the transverse bridging means 50 may comprise overlapping arm members 51a and 51b, each arm member 51a/51b comprising a hook end 52 that interlocks with bridging member receiving apertures or slots 12 disposed in the anterior brace members 21/31. The bridging member receiving slots 12 are preferably provided with projections, teeth, ridges or similar mechanical interlocking members 13 that correspond to and mate with cooperating projections, teeth, ridges or similar mechanical interlocking members 53 disposed on the inner side of the hook ends 52, as illustrated in FIGS. 4 through 6, in order to preclude relative movement between the bridging means 50 to the anterior brace members 21/31.

The sternal closure device 10 is further provided with locking or securing means 60, preferably releasable in the event the sternum 90 needs to be separated in the future, whereby the left and right brace assemblies 20/30 can be brought together and locked or secured in a desired position laterally, typically such that the edges of the sternal halves 91/92 are in abutting relation with the longitudinal sternal incision or kerf 99 closed. In the embodiment of FIGS. 1 through 6, the securing means 60 comprises a threaded bolt 61 mounted in a threaded aperture 63 disposed in the lowermost arm member 51b, with the shaft of the bolt 61 positioned in a slot 62 disposed in the uppermost arm member 51a. A washer flange member 64 is positioned atop the uppermost arm member 51a. Tightening of the bolt 61 forces the two arm members 51a/51b together to preclude lateral movement. Preferably the mutually facing surfaces of the arm members 51a/51b are provided with projections, teeth, ridges or other mechanically interlocking members 54 to further preclude relative lateral movement. Most preferably, the interlocking members 54 are configured in a ratchet-like manner, whereby movement of the arm members 51a/51b to shorten the separation distance between the brace assemblies 20/30 is more readily accomplished than movement to separate the brace assemblies 20/30. Alternatively, the ratcheting members 54 may be structured such that separation of the brace assemblies 20/30 is completely precluded, in which instance additional bolts 61, threaded apertures 63 and the like are not necessary.

Figure 11:
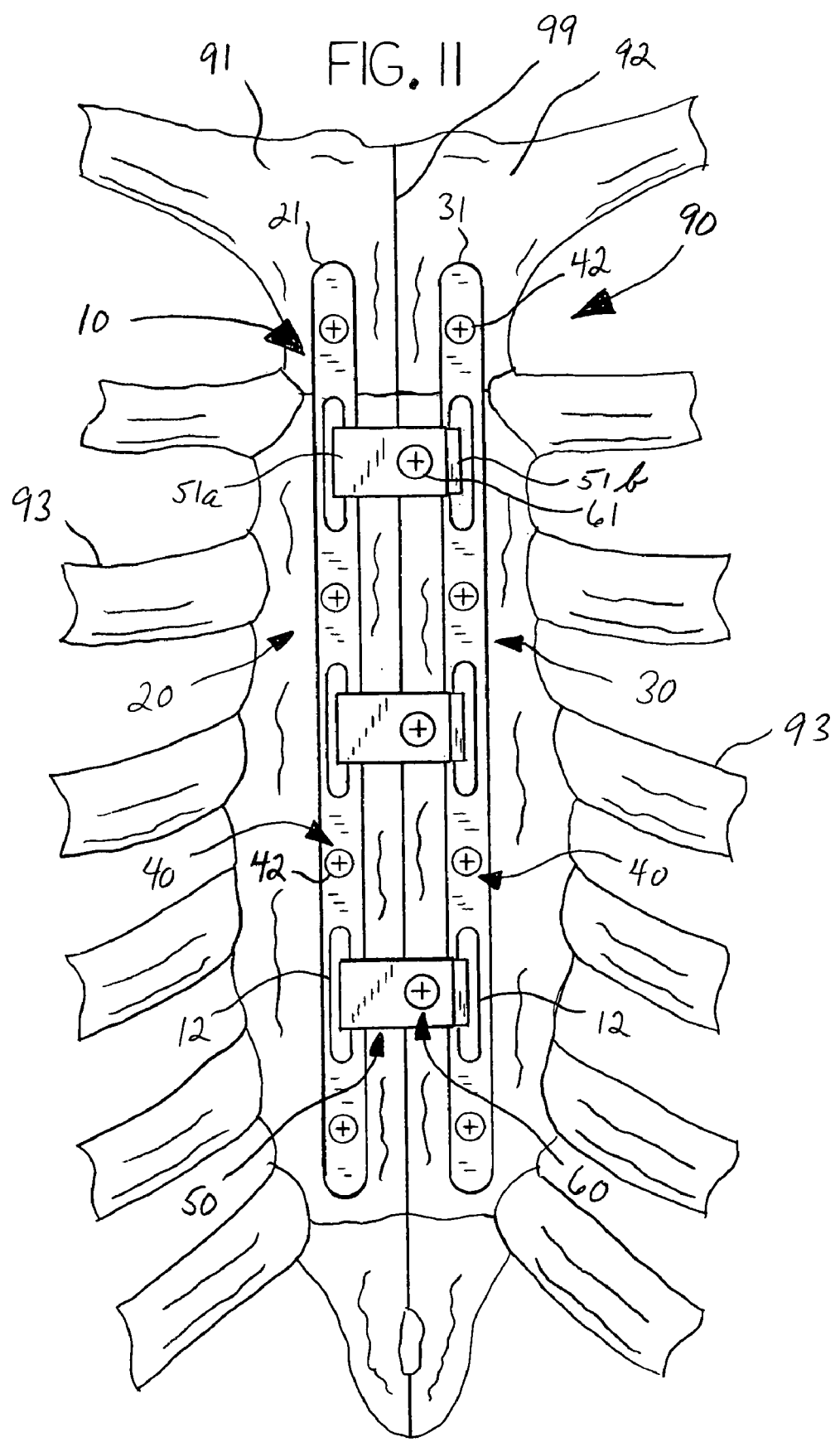
FIG. 11 is a view of an embodiment of the sternal closure device in position on a severed sternum.

To utilize the device, bores are cut into the sternal bone material in each sternal half 91/92. A guide template or the anterior brace members 21/31 themselves may be used to properly position the bores. The posterior brace plates 22/32 are then positioned beneath the sternal halves respectively with the sleeve members 41 inserted up into the bores. The anterior brace plates 21/31 are then positioned on top of the sternal halves 91/92 and the threaded fasteners 42 are threaded into the sleeve members 41, thus defining the two brace assemblies 20/30 such that they are rigidly affixed to the respective sternal halves 91/92. The transverse bridging means 50 are then positioned between the anterior brace members 21/31. The sternal halves 91/92 and the brace assemblies 20/30 are then brought together such that the sternal halves 91/92 abut each other. The securing means 60 is then locked to prevent separation of the brace assemblies 20/30 and the sternal halves 91/92. Should it be necessary to reopen the sternum, the securing means 60 can be released and the transverse bridging means 50 removed. A view of an embodiment showing the sternal closure device 10 in position on the sternum 90 is shown in FIG. 11.

An alternative embodiment for the sternal closure device 10 is illustrated in FIGS. 7 through 10. In this embodiment, at least one of the anterior brace members 21/31 has a different configuration, in that the transverse bridging means 50 comprises lateral arm members 55 affixed rigidly to or formed as an integral component of the anterior brace member 21 or 31. The securing means 60 comprises arm brackets 65 that are secured to the anterior brace member 21 or 31 to receive the lateral arm members 55. The arm brackets 65 are provided with bracket bolts or similar fasteners 66 that are mated with threaded apertures in the anterior brace member 21 or 31, whereby tightening of the bracket bolt 66 forces the arm bracket 65 against the lateral arm member 55 to fix the relative lateral positions of the two brace assemblies 20/30. Preferably, the lateral arm members 55 and either the arm brackets 65 or the upper surface of the anterior brace member 21 or 31 are provided with lateral arm interlocking members 56, such as projections, teeth, ridges or the like. While the illustrations show all lateral arm members 55 extending from only one of the anterior brace members 21/31, i the lateral arm members 55 could extend in opposing directions from both anterior brace members 21/31, with the securing means 60 correspondingly disposed on both anterior brace members 21/31.

The brace assemblies 20/30 of the sternal closure device 10 of this embodiment are affixed to the sternal halves as previously described. When the brace assemblies 20/30 and sternal halves have been brought together, the securing means 60 are locked by tightening the bracket bolts 66, thereby affixing the relative positions of the sternal halves 91/92 and the brace assemblies 20/30.

It is contemplated that equivalents and substitutions to certain elements set forth above may be obvious to those skilled in the art, and therefore the true scope and definition of the invention is to be as set forth in the following claims.

I claim:

1. A sternal closure device comprising:
    a pair of brace assemblies, each said brace assembly comprising a longitudinally extensive anterior brace member and a longitudinally extensive posterior brace member;
    brace joining means connecting said anterior brace member with said posterior brace member in each said brace assembly, wherein said brace joining means comprise threaded sleeve members extending outwardly from said posterior brace members toward said anterior brace members, and threaded fasteners extending through said anterior brace members and mating with said sleeve members;
    transverse bridging means connecting said anterior brace members to each other such that the distance between said anterior brace members is adjustable; and
    locking means securing said brace assemblies in fixed lateral relation to each other.

2. The device of claim 1, wherein said transverse bridging means allows relative movement of said anterior brace members only toward each other.

3. The device of claim 1, wherein said transverse bridging means comprises overlapping arm members.

4. The device of claim 1, wherein said transverse bridging means comprises telescoping arm members.

5. The device of claim 2, wherein said transverse bridging means comprises mechanical interlocking members.

6. The device of claim 5, wherein said mechanical interlocking members are ratcheting members.

7. The device of claim 1, wherein said locking means is releasable.

8. The device of claim 3, wherein said locking means is releasable.

9. The device of claim 1, wherein said brace joining means is such that the distance between said anterior brace member with said posterior brace member is adjustable.

10. The device of claim 1, wherein said transverse bridging means comprise arm members disposed on at least one of said anterior brace members, and wherein said locking means comprise arm brackets mounted on at least one of said anterior brace members, wherein said arm members are received by said arm brackets.

11. The device of claim 6, wherein said transverse bridging means comprise arm members disposed on at least one of said anterior brace members, and wherein said locking means comprise arm brackets mounted on at least one of said anterior brace members, wherein said arm members are received by said arm brackets.

12. A sternal closure device configured for securing the longitudinally severed halves of a sternum in abutting relationship, said device comprising:
    a pair of brace assemblies, each said brace assembly comprising a longitudinally extensive anterior brace member and a longitudinally extensive posterior brace member, wherein said anterior brace members are configured to be disposed on the anterior of said sternal halves and said posterior brace members are configured to be disposed on the posterior of said sternal halves, such that said sternal halves are compressed between said anterior and posterior brace members;
    brace joining means connecting said anterior brace member with said posterior brace member in each said brace assembly, wherein said brace joining means comprise threaded sleeve members extending outwardly from said posterior brace members toward said anterior brace members, and threaded fasteners extending through said anterior brace members and mating with said sleeve members;
    transverse bridging means connecting said anterior brace members to each other in a manner whereby said sternal halves may be brought together in abutting relation; and
    locking means securing said brace assemblies in fixed lateral relation to each other and retaining said sternal halves in abutting relation.

13. The device of claim 12, wherein said brace joining means are configured to be passed through said sternal halves.

14. The device of claim 12, wherein said transverse bridging means allows relative movement of said anterior brace members only toward each other.

15. The device of claim 12, wherein said transverse bridging means comprises overlapping arm members.

16. The device of claim 12, wherein said transverse bridging means comprises telescoping arm members.

17. The device of claim 12, wherein said transverse bridging means comprises mechanical interlocking members.

18. The device of claim 17, wherein said mechanical interlocking members are ratcheting members.

19. The device of claim 12, wherein said locking means is releasable.

20. The device of claim 15, wherein said locking means is releasable.

21. The device of claim 12, wherein said brace joining means is such that the distance between said anterior brace member with said posterior brace member is adjustable.

22. The device of claim 12, wherein said transverse bridging means comprise arm members disposed on at least one of said anterior brace members, and wherein said locking means comprise arm brackets mounted on at least one of said anterior brace members, wherein said arm members are received by said arm brackets.

23. The device of claim 18, wherein said transverse bridging means comprise arm members disposed on at least one of said anterior brace members, and wherein said locking means comprise arm brackets mounted on at least one of said anterior brace members, wherein said arm members are received by said arm brackets.

* * * * *